United States Patent [19]

McEwen et al.

[11] Patent Number: 5,019,243

[45] Date of Patent: May 28, 1991

[54] APPARATUS FOR COLLECTING BLOOD

[76] Inventors: James A. McEwen, 10551 Bamberton Drive, Richmond, British Columbia, Canada, V7A 1K6; William J. Godolphin, 827 West 24th Avenue, Vancouver, British Columbia, Canada, V5Z-2C2; Rainer M. Bohl, 41 East 40th Avenue, Vancouver, British Columbia, Canada, V5W 1L3; Mark N. Dance, 115 West 11th Avenue, Vancouver, British Columbia, Canada, V5Y 1S8; Marty L. Furse, #7 1870 Yew Street, Vancouver, British Columbia, Canada, V6K 3G2; John C. Osborne, 4040 Toronto Street, Port Coquitlam, British Columbia, Canada, V3B 6X8

[21] Appl. No.: 346,065

[22] Filed: May 2, 1989

Related U.S. Application Data

[63] Continuation-in-part of Ser. No. 192,847, May 11, 1988, abandoned, which is a continuation of Ser. No. 33,769, Apr. 3, 1987, Pat. No. 4,828,716.

[51] Int. Cl.$^5$ .......................... B01D 21/26; B01L 3/14
[52] U.S. Cl. ...................................... 210/94; 210/514; 210/516; 210/518; 422/101; 422/102; 494/10; 494/16; 494/19; 494/43
[58] Field of Search .................. 210/94, 97, 513, 514, 210/515, 516, 518, 500.23; 422/101, 102; 494/1, 10, 16, 19, 43

[56] References Cited

U.S. PATENT DOCUMENTS

| | | | |
|---|---|---|---|
| 431,132 | 7/1890 | Wharton | 422/102 |
| 1,480,855 | 1/1924 | Dunkelberger | 422/102 |
| 2,587,221 | 2/1952 | Richardson et al. | 422/102 |
| 3,288,318 | 11/1966 | Corbin et al. | 422/102 |
| 3,508,653 | 4/1970 | Coleman | 210/83 |
| 3,741,400 | 6/1973 | Dick | 210/516 |
| 3,807,955 | 4/1974 | Note, Jr. et al. | 422/102 |
| 3,849,072 | 11/1974 | Ayres | 23/259 |
| 3,852,194 | 12/1974 | Zine, Jr. | 210/516 |
| 3,957,654 | 5/1976 | Ayres | 210/516 |
| 4,021,352 | 5/1977 | Sarstedt | 210/359 |
| 4,046,699 | 9/1977 | Zine, Jr. | 210/516 |
| 4,104,127 | 8/1978 | Bucalo | 435/34 |
| 4,152,270 | 5/1979 | Cornell | 210/516 |
| 4,154,690 | 5/1979 | Ballies | 210/516 |
| 4,189,382 | 2/1980 | Zine, Jr. | 210/782 |
| 4,202,769 | 5/1980 | Greenspan | 210/83 |

(List continued on next page.)

FOREIGN PATENT DOCUMENTS 0100664  2/1984  European Pat. Off. ............ 422/102
2137854  2/1973  Fed. Rep. of Germany ...... 422/102

OTHER PUBLICATIONS

Brochure by Sarstedt entitled "Monovette With Luer-Cone" (3 pages).

Primary Examiner—W. Gary Jones
Attorney, Agent, or Firm—Klarquist, Sparkman, Campbell, Leigh & Whinston

[57] ABSTRACT

Apparatus for collecting a sample of liquid, such as blood, having a plurality of phases of differing densities. Disclosed is an apparatus for collecting a sample in an enclosed chamber, wherein said apparatus can be used with a separating means which rotates the chamber about either a longitudinal axis of the chamber, or about an axis perpendicular to the longitudinal axis of the chamber and not passing through the chamber. In addition, said apparatus facilitates automated manipulation of the sample by providing formed features for: decreasing the gas permeability of said apparatus; clot activation of a blood sample contained within said apparatus; interconnection of a multiplicity of said apparatus; automated manipulation of said apparatus; protecting markings upon said apparatus; layering the construction of said apparatus; and, encoding of information upon said apparatus in both a tactile and visual manner. Also disclosed is an apparatus for dispensing fluid from said enclosed chamber.

3 Claims, 8 Drawing Sheets

U.S. PATENT DOCUMENTS

| | | | |
|---|---|---|---|
| 4,214,020 | 7/1980 | Ward et al. | 210/500.23 |
| 4,294,707 | 10/1981 | Ikeda et al. | 210/516 |
| 4,310,488 | 1/1982 | Rahm et al. | 422/102 |
| 4,336,288 | 6/1982 | Leddy | 422/102 |
| 4,350,593 | 9/1982 | Kessler | 210/516 |
| 4,369,117 | 1/1983 | White | 210/782 |
| 4,397,897 | 8/1983 | Schülke | 422/102 |
| 4,417,981 | 11/1983 | Nugent | 210/209 |
| 4,425,235 | 1/1984 | Cornell et al. | 210/516 |
| 4,438,198 | 3/1984 | Schmer | 435/178 |
| 4,443,345 | 4/1984 | Wells | 210/782 |
| 4,464,254 | 8/1984 | Dojki et al. | 210/136 |
| 4,492,634 | 1/1985 | Villa-Real | 210/398 |
| 4,602,995 | 7/1986 | Cassaday et al. | 210/120 |

APPARATUS FOR COLLECTING BLOOD

REFERENCE TO RELATED APPLICATION

This is a continuation-in-part of U.S. patent application Ser. No. 07/192,847 filed May 11, 1988, now abandoned, which was a continuation of U.S. patent application Ser. No. 07/033,769 filed April 3, 1987, now U.S. Pat. No. 4,828,716.

FIELD OF THE INVENTION

The present invention refers to an apparatus for collecting, separating and manipulating a sample of liquid such as blood contained in a chamber. In particular, the invention pertains to apparatus for collecting a blood sample in a tubular chamber, manipulating the sample, and separating the phases of the blood sample.

BACKGROUND OF THE INVENTION

Blood to be analyzed for diagnostic and monitoring purposes is customarily collected by venipuncture through a cannula or needle attached to an evacuated glass collection tube. Tubes are labelled and transported to the laboratory where they are identified, recorded and prepared for analysis. Separation of the serum or plasma phases from the blood cells is often necessary for laboratory analysis and is usually carried out by centrifugation. Once separated the phases are best kept in an inert container, physically and chemically isolated, to avoid disturbance of analyte concentrations. Some analytes may have specific requirements such as constant or low temperature, or shielding from light. The blood may contain infectious agents and should be kept isolated, preferably in a closed system to reduce exposure to laboratory personnel. Serum and plasma are commonly used analytical samples. If serum is desired the specimen must be permitted to clot or coagulate before further separation is attempted. If plasma is desired the specimen must have an anticoagulant mixed with it immediately after collection. For this purpose anticoagulant materials are commonly placed in blood collection devices at the time of manufacture.

Specimens which have been centrifuged are often subsequently aliquotted. Aliquotting is the process of dividing up samples for distribution among analyzer sites. This involves the transfer of analyte from the collection tube to one or more secondary containers. These secondary containers may be standard test tubes or custom sample cups for specific analyzers. To make the blood processing procedure efficient and safe collection tubes must offer containment, additives, identification and ease of handling.

The popular pre-evacuated blood collection tube (such as described by Kleiner U.S. Pat. No. 2,460,641) has the following advantages: once sterilized, its interior remains sterile without additional packaging; simplicity of structure and use, in that its basic form consists of only a glass tube permanently closed at one end with a rubber stopper in the open end; and it is self-healing when blood drawing is complete and the cannula which was used to puncture the rubber stopper has been removed. Such collection tubes are typically made of glass and are thus susceptible to breakage. Collection tube breakage is a very dangerous event because it may scatter sharp pieces of blood contaminated glass that may contain infectious agents such as the viruses associated with Acquired Immune Deficiency Syndrome or Hepatitis. A common mode of infection of laboratory and hospital staff is skin laceration by needles or broken glass.

One method of reducing the hazards associated with breakage is to coat the glass with plastic. Glass bottles coated with plastic are sold by the tradenames "Safemor" by Mallinckrodt Inc., "Safe-Cote" by Fisher Scientific Company of Pittsburgh, Pa, and "Second Skin" by Wheaton Safety Container Company of Mays Landing, NJ. Also found are plastic coated incandescent light bulbs, so coated to reduce hazards associated with explosion of the bulb. Plastic-coated glass exhibits increased strength over regular uncoated glass, thus reducing breakage. If the glass does break, the plastic contains both the glass fragments and the liquid within. However, these containers cannot be used to collect or process a sample of blood and are not intended for such use.

An alternative to coating a glass tube with plastic is to construct the whole tube from plastic. Unfortunately, while plastics have high breakage resistance few are capable of holding a vacuum over long periods of time (most manufacturers specify a 2 year shelf life for their evacuated glass tubes, and the International Standards Organization specifies that the volume of water drawn by an evacuated tube shall not deviate more than 10% before the tube's expiry date). Sarstedt Inc. produces a plastic tube, the "Monovette", but because of its poor vacuum retention it is used like a syringe and is not considered a convenient means of routine blood collection. Tzafon markets a plastic, evacuated blood collection tube under the tradename "Vacuette", but it cannot hold a vacuum over a prolonged period of time without external overpacking which must be removed prior to tube use. One object of this invention is to combine the properties of shatter resistance and vacuum retention in a single plastic tube which is easy to manufacture and use.

While breakage is a relatively infrequent event aliquotting is a routine procedure with similar associated hazards. Presently there are a number of aliquotting methods. A common method is to remove the stopper and use a dropper pipette to transfer some of the sample from the open primary tube to a secondary container. This procedure is hazardous: removal of the stopper generates infectious aerosols, and an open sample tube may easily be spilled. Another common method of aliquotting is to simply decant from the opened primary tube into secondary containers. This is even more hazardous because skill is required to decant a small amount of serum or plasma without spillage.

Some devices have been made which attempt to address these hazards. One such device is made by Helena Laboratories of Beaumont, Texas and sold by the tradename "Tip-Top" Dispenser Cap. The Tip Top dispenser is fastened to the open end of a centrifuged blood collection tube, inverted and squeezed to dispense a sample through an orifice to a sample cup. The major difficulty with the Tip Top dispenser and others like it is that it requires the hazardous step of stopper removal from the blood collection tube. A device which does not require stopper removal is made by Clean Tech SCI AG of Langenthal Switzerland and sold by the tradename "The CleanTech System". The CleanTech system consists of several components including a cannula to puncture the stopper, a machine to insert the cannula into the stopper, a pipette to access the sample through the stopper and a pump which fastens to the pipette to draw the sample from the tube. This device addresses many of the hazards of dispensing a sample but it is relatively complex, expensive and requires several steps to use. Another objective of this invention is to fill the need for an apparatus which allows blood to be contained and dispensed without risk of contamination or spillage through removal or handling of the stopper.

The work volume, both in number of blood specimens and number of tests (hence, aliquots) performed by typical clinical laboratories is rapidly increasing. This has greatly increased the likelihood of sample missidentification. Missidentified samples compromise patient care. Most blood collection tubes have paper labels affixed to their sides where the sample identification data can be handwritten. Identification in this manner is a time consuming and awkward task as it is difficult to write on a small, curved surface. The markings may get rubbed off through handling or obscured by foreign matter. In addition, mistakes can be made due to faulty transcription or illegible handwriting.

One alternative is to use pressure-sensitive labels. These labels change color in response to localized pressure. The markings are thus a part of the label and cannot be rubbed off. Such labels still suffer from the drawbacks of awkwardness, time consumption and human error.

Another alternative is to use barcodes, magnetic strips, or some other type of machine-readable label. These labels can be scanned by machine more quickly and with greater accuracy than a human can read handwriting. Such labels are relatively resistant to stains and abrasion and are unlikely to be misread if damaged. The main drawbacks are that such labels cannot be produced manually on site nor can they be easily read and interpreted by humans. A further objective of this invention is to provide sample identification which is simple, accurate, durable and both machine and human readable.

A blood specimen must be clotted to yield serum. Activation of the formation of this clot results as a consequence of contact with the glass collection tube in which the blood was collected and can be enhanced by the addition of various clot-activating materials as described in U.S. Pat. No. 4,189,382 by Zine. The National Committee for Clinical Laboratory Standards (NCCLS) recommends a waiting time of 20 to 30 minutes for clot formation to occur with no additives. If thrombin or silica particles are used as clotting activators, the NCCLS recommends 5 minute or 15 minute waiting times, respectively. The clotting process is much slower in conventional plastic tubes due to the difference in surface characteristics between glass and plastic. It is therefore necessary to add clot activators to initiate clotting in a plastic tube thus increasing the cost of the tube. Another objective of this invention is to provide a tube with integral clot activation such that the clotting process is initiated and enhanced without the addition of a clotting additive.

With the advent of high speed biochemical and chemical analyzers, the bulk of time and effort spent in a typical clinical laboratory in processing blood samples has shifted to the collection and preparation stages. Further gains in processing efficiency will be obtained by improving the handling characteristics of blood collection tubes.

One of the main obstacles to efficient specimen handling is the use of multiple blood collection tube sizes. The smaller tubes, often used to collect blood from children, are difficult to handle and have very little space on which to record sample identification information. The variation in tube size leads to nonuniform packaging and requirements for different sized test-tube racks. In modern blood analyzers there is a design trend towards systems which sample directly from blood collection tubes (primary tube sampling). The Hitachi-737 analyzer is one of the first of this type. Hence it is necessary to adapt the analyzer to whatever tube size is used to contain the specimen. Since most laboratories receive mixed batches of varying tube sizes, the analyzers must either be adjusted manually at great labor cost or automatically at great equipment cost.

Concurrent with the trend towards primary tube sampling is a trend towards automated sample handling. Procedures for blood separation and analysis expose laboratory personnel to infectious agents that may be passed through contact with blood; e.g. hepatitis or acquired immune deficiency syndrome. In addition, conventional batch processing of blood specimens is labor-intensive and has not generally been automated whereas other processes in clinical laboratories have. Automation of blood separation can effectively isolate laboratory personnel from the dangers of blood processing while theoretically increasing the speed of the overall analytical procedure.

A highly automated system would incorporate a robotic manipulator, automatic identification, and primary tube sampling analyzers. Automatic identification may require the tube to be manipulated in a very specific orientation, while some analyzers may require the exertion of a large insertion force along the tube's axis to seat it in the sampling bay. Present blood collection tubes are suboptimal for automatic manipulation because they have smooth, uniform outer surfaces. This makes it difficult for a robot to grip tubes firmly and repeatably with correct orientation.

A syringe has two of the characteristics needed for efficient sample handling. First, it has a single external size, regardless of the volume of blood drawn. Second, it has flanges on its exterior which could accommodate robotic gripping and orientation. Syringes are relatively inconvenient to use compared with evacuated collection tubes. This problem is addressed by Sarstedt's Monovette, which is a syringe-like collection tube with a plunger handle which can be removed after the blood is drawn and afterwards handled like a tube. This device, however, is less amenable to handling with an automated device than an evacuated collection tube. A further objective of this invention is to provide tubes which are more amenable to both human and automatic handling.

Co-pending U.S. application Ser. No. 07/033,769 by McEwen et al describes a method of separating a sample of blood contained in a tubular chamber wherein the tubular chamber and its contents are rotated about the chamber's longitudinal axis and providing a means of processing a sample of blood having the features of: ability to separate the blood phases under conditions which limit personnel exposure; maintenance of these phases separated and unchanged; monitoring of gross characteristics of the phases; ready adaptability to varying blood collection requirements; and flexibility for stand-alone use or integration into automated systems. The present invention provides an improved blood collection and separation device and provides an apparatus to dispense a portion of the separated blood sample separated in the blood collection and separation device according to the invention of McEwen et al as described in co-pending U.S. patent applications Ser. No. 07/033,769 and serial number 07/192,847. U.S. patent applications Ser. No. 07/033,769 and 07/192,847 are herein incorporated by reference.

SUMMARY OF THE INVENTION

The present invention provides an apparatus for collecting a sample of liquid such as blood comprising: a tubular chamber which initially contains a partial vacuum, and into which a sample of liquid may be drawn; and a geometric feature attached to said tubular chamber which facilitate automated manipulation of the apparatus.

The present invention also provides an apparatus for collecting a sample of liquid such as blood comprising: a tubular chamber which initially contains a partial vacuum, and into which a sample of liquid may be drawn; and includes a means of enhancing the properties of said apparatus which defines a layer irremovably attached to said tubular chamber.

Other objects of the present invention include forming said tubular chamber to provide: a raised feature to facilitate automated manipulation of the sample collection apparatus; an interconnection means to allow a multiplicity of sample collection apparatus to be removably connected together; a means of enhancing the gas impermeability of said tubular chamber; a means of enhancing clotting of a blood sample contained inside said tubular chamber; and a means of protecting identification markings made upon said tubular chamber.

The present invention consists of: an apparatus comprising an evacuated, tubular chamber, blood collection device, which can be used in a conventional manner with available blood collection cannulae to collect a blood sample, and contains clot activation materials, chemical additives, or anticoagulants as required; a means of enhancing properties of the apparatus by layered construction of said tubular chamber; and, a means of facilitating automated manipulation of said apparatus by irremovably attaching features to said tubular chamber that allow a multiplicity of apparatus to be connected together, or allow an automated gripper to grasp said apparatus and apply an axial force to said apparatus without slipping.

The invention also provides an encapsulated sample collection apparatus from which the closure cannot be removed and which decreases the safety hazards associated with such closure removal.

DESCRIPTION OF SPECIFIC EMBODIMENTS

This application provides apparatus which enable the collection of blood samples by venipuncture and separation of the blood samples by centrifugation. Additionally, the apparatus provide features which facilitate the processing of the collected blood sample in an automated manner. For clarity and simplicity each feature is presented in a specific embodiment although they may be combined as function dictates. To assist venipuncture collection, the apparatus disclosed may be evacuated prior to such collection. Referring now to the drawings, FIGS. 1 through 8 show the specific embodiments which illustrate the features of this invention.

Figure 1:
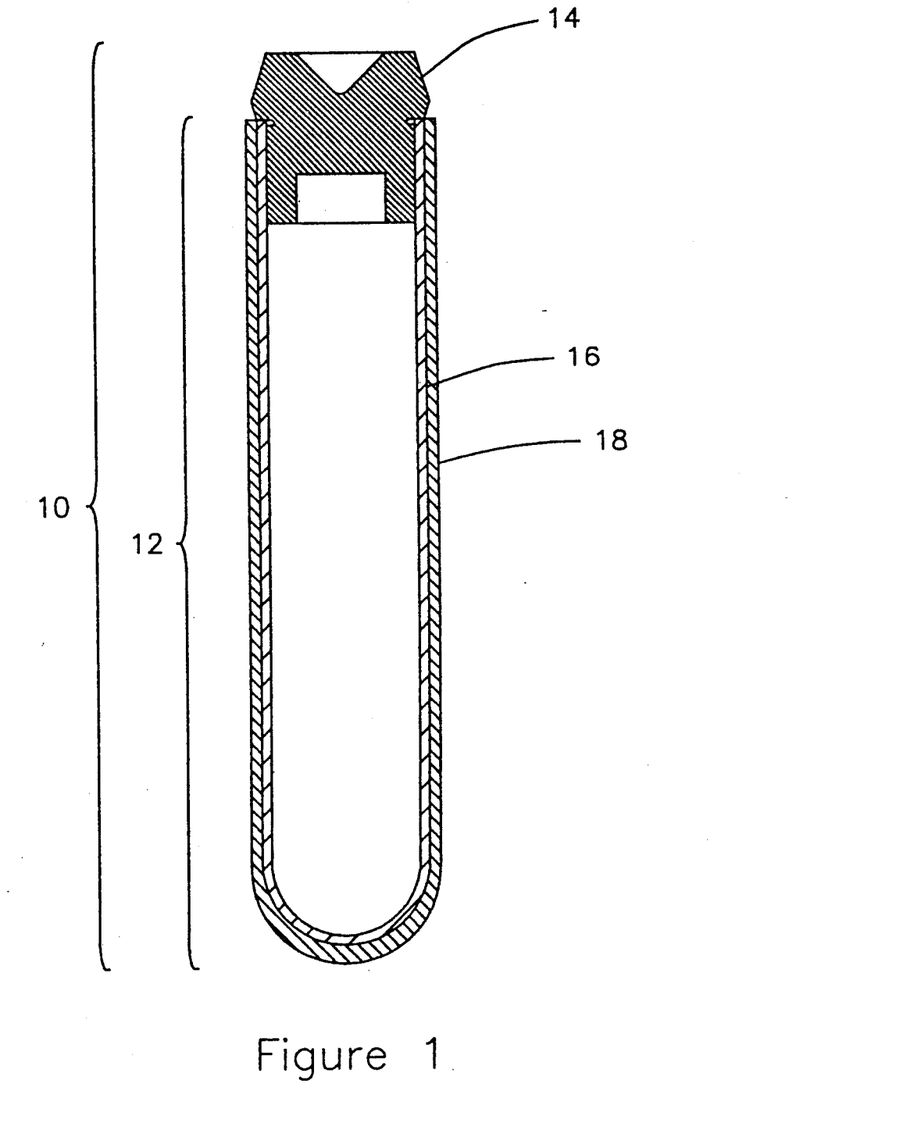
FIG. 1 is a sectional view of a layered sample collection apparatus.

The layered sample collection apparatus 10 shown in FIG. 1 consists of tubular chamber 12 and closure 14. Layered sample collection apparatus 10 illustrates the layered construction of a blood collection device through which features that facilitate automated manipulation of blood collection apparatus may be realized.

Tubular chamber 12 has a closed end and an open end shaped to receive and be sealed by closure 14. Said tubular chamber 12 comprises interior layer 16 and exterior layer 18 which are irremovably connected. In this embodiment, interior layer 16 is constructed of a stiff, substantially transparent material such as glass or polystyrene and exterior layer 18 is constructed of a substantially transparent, barrier plastic such as that sold by E.I. Du Pont de Nemours Inc. under the tradename Selar Pa. One method of forming exterior layer 18 is to dip interior layer 16 into a bath of molten material such as Selar Pa thereby depositing a layer of molten material upon said interior layer. Cooling interior layer 16 and the deposited material forms exterior layer 18. By way of the specific construction of interior layer 16 and exterior layer 18, tubular chamber 12 is substantially translucent and may be pre-evacuated to assist in sample collection. Advantageously, the required thickness of exterior layer 18 is determined solely by the desired barrier characteristics of tubular chamber 12 and not by any other mechanical characteristic of said tubular chamber. As a result of this a minimum volume of barrier material is required in the construction of said tubular chamber 12. This is desirable because barrier materials, especially barrier plastics, are generally more expensive to employ for the construction of commodity items, such as blood collection tubes, then more common injection-moldable materials.

Closure 14 is preferably constructed of a self-healing, medical grade, brominated butyl rubber. Said closure forms a seal with the inside wall of interior layer 16 adequate to allow tubular chamber 12 to be pre-evacuated.

Although in this embodiment tubular chamber 12 is constructed from two separate layers attached one to another, it is contemplated that tubular chamber 12 may be initially constructed of a homogeneous plastic material which may later be modified to create a multiplicity of regions where the composition of this originally homogeneous plastic has been altered to exhibit different properties. For example, modification of the homogeneous plastic at the inner or outer surfaces of tubular chamber 12 may lead to the creation of new materials in the surface layers of said tubular chamber which exhibit the properties of substantial translucence or gas impermeability. Modification of the homogeneous plastic used to form tubular chamber 12 may be accomplished by the heating said homogeneous plastic in an environment containing chemicals or compounds which are to be integrated into the polymer structure of the homogeneous plastic. Such heating of said tubular chamber could be accomplished with energy from a low power laser.

FIGS. 2a through 2d show encapsulated sample collection apparatus 30 a second embodiment of this invention. Said encapsulated sample collection apparatus consists of internal tubular chamber 32, closure 34, and covering layer 36. Encapsulated sample collection apparatus 30 is a blood collection device from which the closure may not be removed.

Figure 2A:
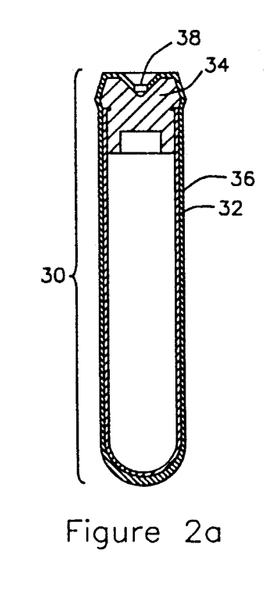
FIG. 2a is a sectional view of an encapsulated sample collection apparatus.

Internal tubular chamber 32 has a closed end and an open end shaped to receive closure 34. Said internal tubular chamber 32 is constructed of a substantially transparent material such as glass or polystyrene.

Closure 34 is preferably constructed of a self-healing, medical grade, brominated butyl rubber and forms a seal with the inside wall of internal tubular chamber 32 adequate to prevent fluid from being interposed between the circumference of said closure and the surface of said internal tubular chamber.

Substantially covering the exterior surface of internal tubular chamber 32 and the exposed surface of closure 34 save for a small uncovered region 38 on the axis of said closure is covering layer 36. Said covering layer is constructed of a substantially transparent, barrier plastic such as that sold by E.I. Du Pont de Nemours Inc. under the tradename Selar Pa, after said closure is inserted into the open end of said internal tubular chamber. Construction of said covering layer may be accomplished by dipping internal tubular chamber 32 into a bath of molten material, such as Selar Pa, and cooling the molten material deposited by such dipping thereby creating said covering layer. During the dipping procedure internal tubular chamber 32 may be supported by closure 34 which is grasped at uncovered region 38 upon said closure. In order to evacuate the interior of encapsulated sample collection apparatus 30, assembly of said apparatus may occur in a vacuum.

Figure 2B:
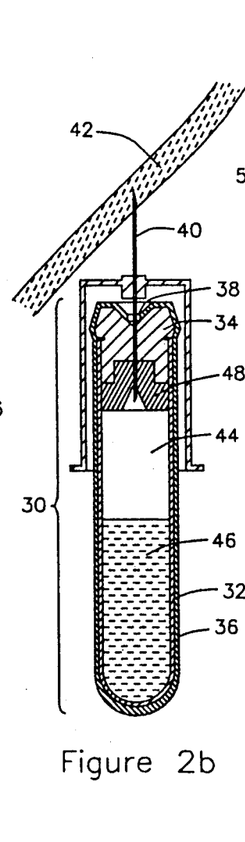
FIG. 2b shows encapsulated sample collection apparatus being used to collect a blood sample from a blood vessel.

FIG. 2b shows encapsulated sample collection apparatus 30 in use. Encapsulated sample collection apparatus is used to collect blood in a manner identical to that of conventional evacuated blood collection tubes, that is, one end of double-sided venipuncture needle 40 is inserted into blood vessel 42 and the other end of said needle pierces closure 34 thereby entering sample collection volume 44. Uncovered region 38 permits venipuncture needle 40 to pass through closure 34 without passing through covering layer 36. Once venipuncture needle 40 has reached said sample collection volume, blood sample 46 from the vessel flows into said sample collection volume. In practice encapsulated sample collection apparatus 30 may further include separation means 48, disposed inside internal tubular chamber 32 prior to the addition of covering layer 36, to facilitate separation of blood sample 46. Said separation means may consist of an intermediate density silicone gel similar to that employed by Zine in U.S. Pat. Ser. No. 3,852,194 or a plug-like-separator similar to that employed by Coleman in U.S. Pat. Ser. No. 3,508,653. The disposition of separation means 48 inside internal tubular chamber 32 depends upon the construction of said separation means, i.e. if said separation means consists of an intermediate density gel then it is best disposed at the end of internal tubular chamber 32 opposite closure 34, however, if said separation means is constructed similar to the plug-like-separator of Coleman then it is best fastened to closure 34.

Figure 2C:
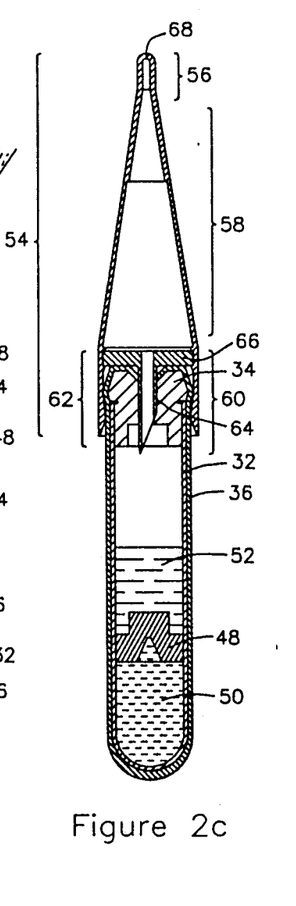
FIG. 2c shows encapsulated sample collection apparatus with an attached fluid dispensing apparatus provided by this application.

The addition of a separation means as described above facilitates the centrifugal separation of the cellular component of said blood sample when encapsulated sample collection apparatus 30 is rotated around either its own longitudinal axis or some other axis. The result of this centrifugal separation is shown in FIG. 2c. Cellular component 50 has been partitioned inside said internal tubular chamber and has been separated from non-cellular component 52 by separation means 48. Non-cellular component 52 may be taken directly from internal tubular chamber 32 by an automated sampler which pierces closure 34 or, as shown in FIG. 2c, fluid dispensing apparatus 54 may be attached to said encapsulated sample collection apparatus to permit manual dispensing. Fluid dispensing apparatus 54 provides a means of dispensing a sample from the sample collection and separation apparatus of the present invention in such a way that removal of closure 34 is not required. Fluid dispensing apparatus 54 comprises dispensing tip 56, conical bulb 58, flexible skirt 60 and pipette insert 62. Pipette insert 62 includes hollow spike 64 and solid backplate 66 and is preferably formed as one piece out of a plastic such as high-impact styrene. Hollow spike 64 allows fluid exchange between the interior of the encapsulated sample collection apparatus 30 and the interior of the conical bulb 58 and thereby provides a path for fluid contained in encapsulated sample collection apparatus 30 to enter conical bulb 58. The extreme edge of solid backplate 66 seals against the walls of conical bulb 58 so as to keep fluid contained within said bulb from leaking around solid backplate 66. Dispensing tip 56 is integral to conical bulb 58 and includes orifice 68 preferably 0.38 to 0.51 millimeters in diameter which extends from the interior of conical bulb 58 to exterior of dispensing tip 56. Dispensing tip 56, conical bulb 58 and flexible skirt 60 are preferably formed as one piece out of a plastic such as polypropylene.

In use, fluid dispensing apparatus 54 is attached to encapsulated sample collection apparatus 30 after blood sample 46 has been separated. Hollow spike 64 is pushed through covering layer 36 and closure 34, so that solid backplate 66 is seated against closure 34. Once fluid dispensing apparatus 54 is attached to encapsulated sample collection apparatus 30, the entire assembly may be inverted and fluid contained inside internal tubular chamber 32 may be dispensed by repeatedly squeezing conical bulb 58. The size of orifice 68 in dispensing tip 56 is such that the fluid in encapsulated sample collection apparatus 30 is readily dispensed in a semi-continuous stream.

Advantageously, the hazards associated with the removal of closures from blood collection tubes are reduced by this embodiment because closure 34 may not be removed from internal tubular chamber 32. A second advantage of encapsulated sample collection apparatus 30 exists in the simplified function of closure 34 which no longer needs to be stiff enough to withstand manual removal from internal tubular chamber 32. With this function no longer required of closure 34, said closure acts simply as a self-sealing port through which blood is drawn and components of said blood are extracted. In turn, this simplified function allows the construction of said closure to be simplified.

Figure 2D:
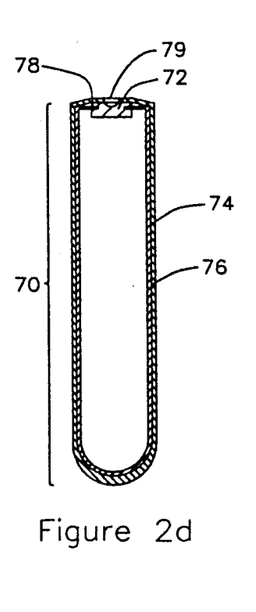
FIG. 2d shows an alternate version of the encapsulated sample collection apparatus.

FIG. 2d shows further encapsulated embodiment 70 comprised of internal tubular chamber 74, covering layer 76 and self-sealing plug 72 which replaces closure 34 of the previous embodiment. Internal tubular chamber 74 has a closed end and an open end. The open end of said internal tubular chamber includes inner flange 78 shaped to receive a circumferential groove formed into self-sealing plug 72. Said internal tubular chamber 74 is constructed of a substantially transparent material such as glass or polystyrene perhaps by blow-molding techniques.

Substantially covering the exterior surface of internal tubular chamber 74 and the exposed surface of self-sealing plug 72 save for a small uncovered region 79 on the axis of said self-sealing plug is covering layer 76. Said covering layer is constructed in a similar manner to covering layer 36 of FIGS. 2a through 2c.

Self-sealing plug 72 is preferably constructed from a similar self-healing, medical grade, brominated butyl rubber as closure 34. By modifying the function of closure 34 said self-sealing plug may be constructed in a simpler shape and from a smaller volume of self-sealing material, which is advantageous when the self-sealing material is difficult to form or otherwise expensive to produce.

Figure 3A:
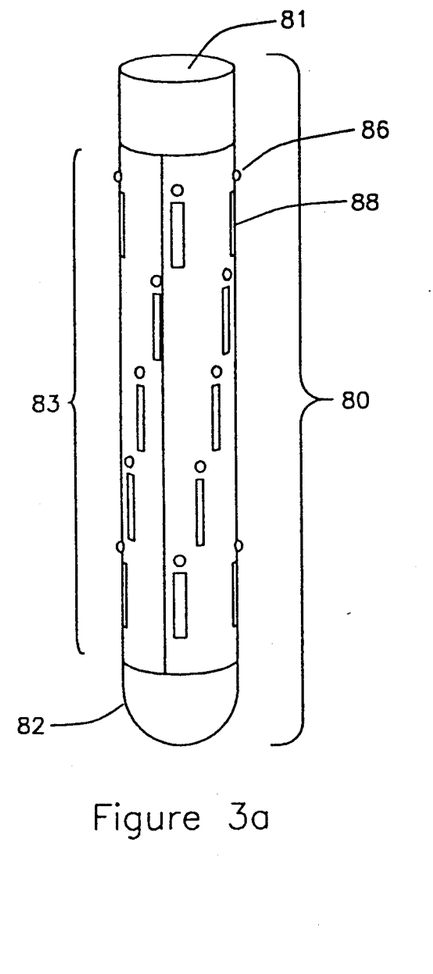
FIG. 3a is a sectional view of an adaptable sample collection apparatus showing a collection tube with a modifiable outer covering.
Figure 3B:
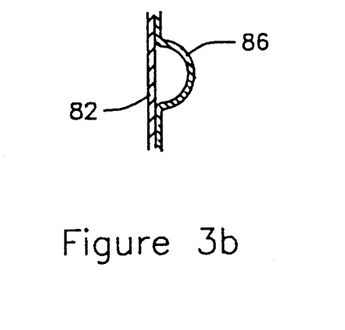
FIG. 3b is an enlarged sectional view of a surface feature of the adaptable sample collection apparatus.
Figure 3C:
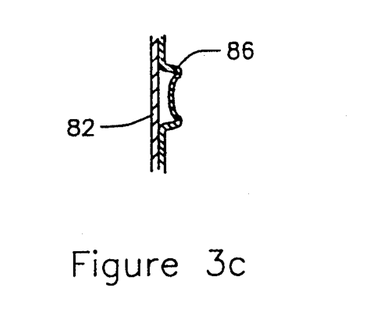
FIG. 3c is an enlarged sectional view of a deformed surface feature of the adaptable sample collection apparatus.

FIGS. 3a through 3c illustrates adaptable sample collection apparatus 80 which is another embodiment of this invention. Adaptable sample collection apparatus 80 comprises closure 81, tubular chamber 82 and modifiable overlaying layer 83 irremovably attached to tubular chamber 82. Closure 81 is similar to closure 14 shown in FIG. 1. Tubular chamber 82 has a closed end and an open end shaped to receive and be sealed by closure 81 and is preferably constructed of a stiff, substantially transparent material such as glass or polystyrene Said modifiable overlaying layer allows information to be formed onto or retrieved from said adaptable sample collection apparatus by automated or manual means. Modifiable overlaying layer 83 is preferably constructed from a thin translucent, plastic sheet which has been formed to incorporate a multiplicity of surface features 86. Surface features 86 are constructed such that each may be irreversibly deformed thereby encoding binary information into said surface feature because surface features 86 exists in either a undeformed or deformed state. Deformation of surface feature 86 may consist of crushing surface feature 86 inwards upon itself as illustrated in FIGS. 3b and 3c. As described, surface features 86 provide both visual and tactile indication of their state.

Printed onto modifiable overlaying layer 83 beside each surface feature 86 is printed information 88 which can be used to attach significance to each surface feature. As a specific example, printed information 88 may indicate the presence of a chemical additive in adaptable sample collection apparatus 80. Deformation of surface feature 86 beside printed information 88 would indicate that this chemical additive is indeed present.

Figure 4:
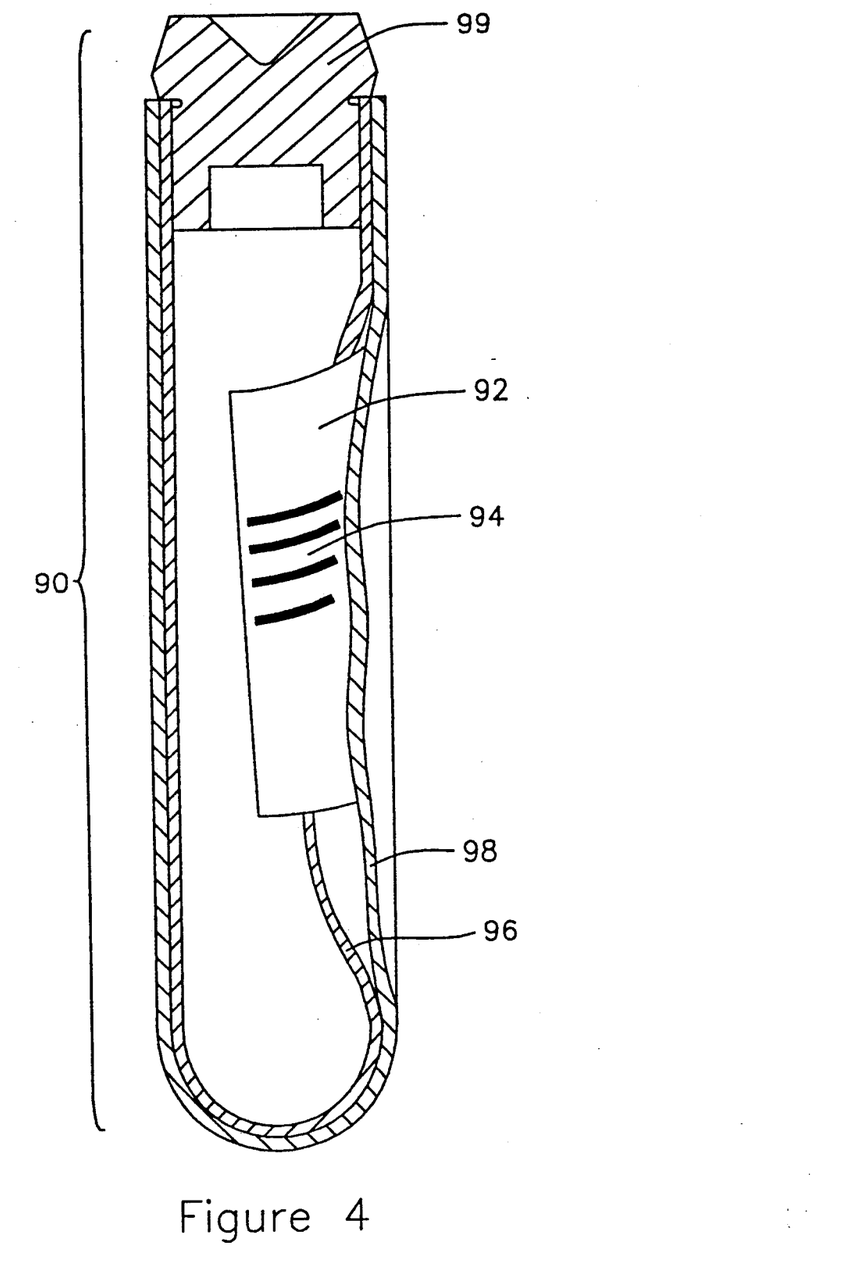
FIG. 4 is a sectional view illustrating the embedded identification of a sample collection and identification apparatus.

FIG. 4 shows sample collection and identification apparatus 90 which comprises interior layer 96, exterior layer 98, closure 99 and identification means 92. Interior layer 96, exterior layer 98 and closure 99 are similar to interior layer 16, exterior layer 18 and closure 14 respectively of layered sample collection apparatus 10 shown in FIG. 1.

Identification means 92 is preferably interposed between interior layer 96 and exterior layer 98 at the time of construction of said sample collection and identification apparatus. Identification means 92 is preferably constructed from a thin, flexible material which accepts printed markings such as paper and is bonded to interior layer 96 prior to the addition of exterior layer 98. Exterior layer 98 may be created by dipping as previously disclosed. Said identification means includes human or machine-readable markings 94 which encode information about sample collection and identification apparatus 90. Advantageously, the layered construction of said sample collection and identification apparatus protects said identification means 92 from damage or removal.

Figure 5A:
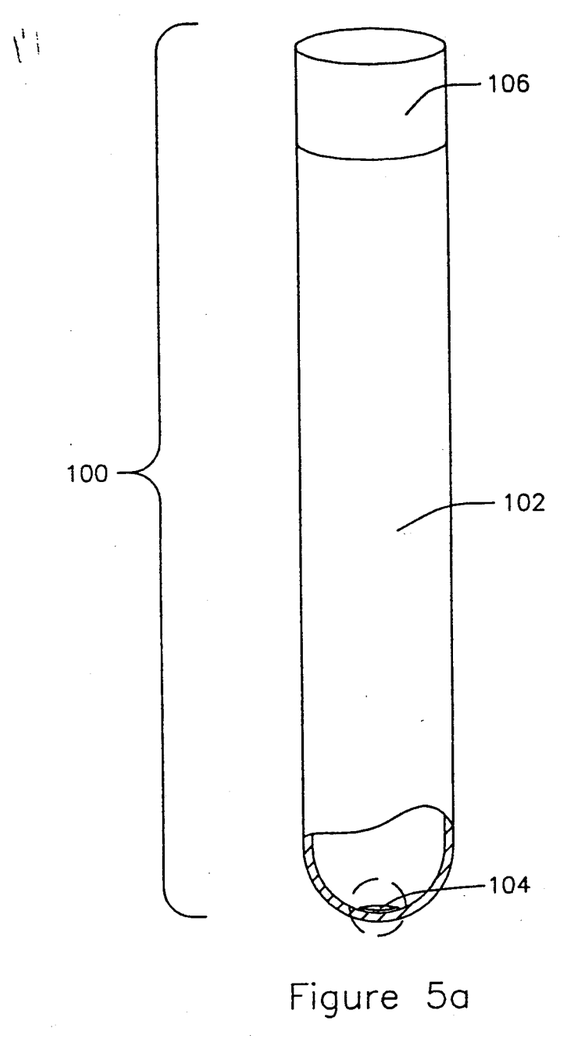
FIG. 5a is a sectional view of a sample collection and clot activation apparatus.
Figure 5B:
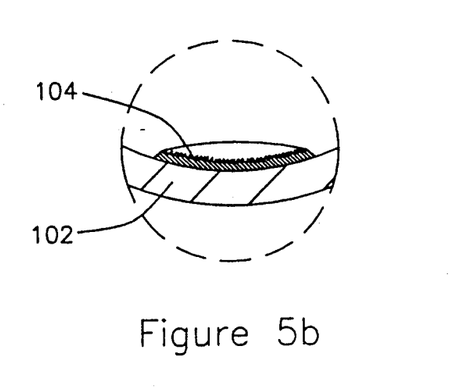
FIG. 5b is an enlarged view of the clot activation surface present on the interior of the sample collection and clot activation apparatus.

FIGS. 5a and 5b show sample collection and clot activation apparatus 100 which consists of tubular chamber 102 and closure 106. Closure 106 is similar to closure 14 shown in FIG. 1.

Tubular chamber 102 has a closed end and an open end shaped to receive and be sealed by closure 106 and incorporates clot activation region 104 on its interior surface. Tubular chamber 102 is preferably constructed of a substantially transparent material such as glass or a substantially transparent barrier plastic such as that sold by E.I. Du Pont de Nemours Inc. under the tradename Selar Pa.

FIG. 5b shows an enlarged view of said clot activation region. Clot activation region 104 preferably consists of an area located at the closed end of tubular chamber 102. The area occupied by clot activation region 104 should not exceed one third the total interior surface area of tubular chamber 102 so as to prevent clot formation in and adherence to regions where the non-cellular portion of a collected blood sample will reside following centrifugation. Clot activation region 104 is formed with a surface texture which precipitates clot formation in blood. As a specific example, a surface finish with both roughness height and roughness width in the range of 0.4 to 20 microns provides a good clot activation surface. Clot activation region 104 may be created on the inside surface of tubular chamber 102 with secondary finishing operations such as roughening the surface with an abrasive tool or sand-blasting the region.

Figure 6A:
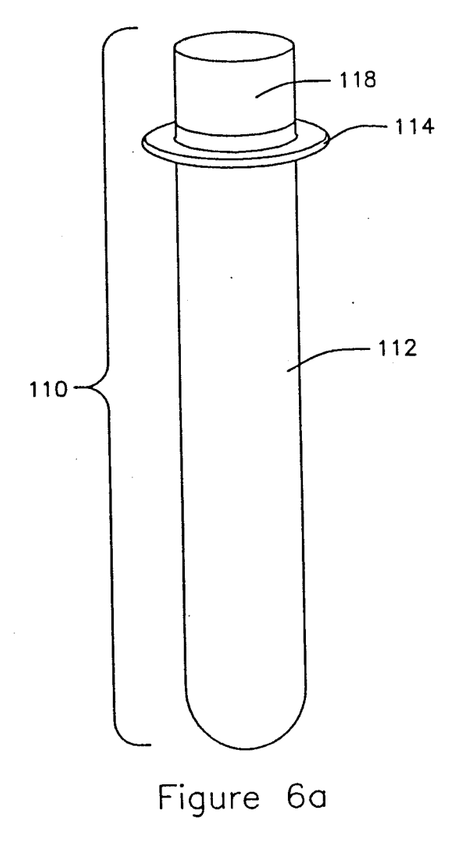
FIG. 6a shows a grippable sample collection apparatus which provides a means for automated devices to grip and manipulate a sample.
Figure 6B:
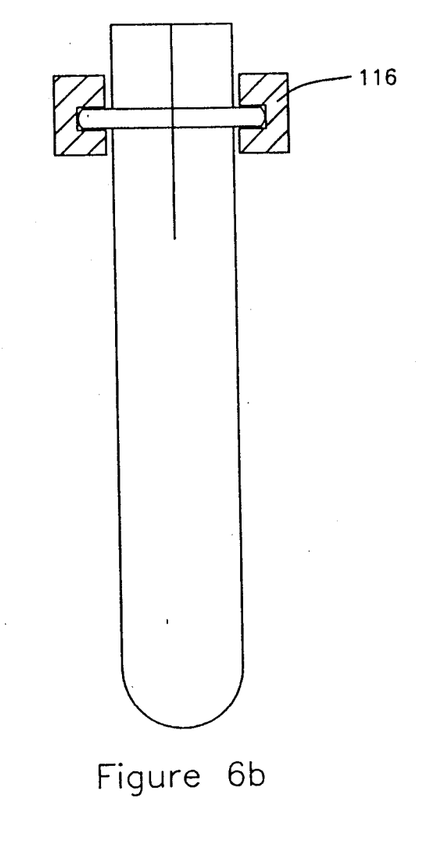
FIG. 6b shows how the grippable sample collection apparatus would be grasped by a robotic or automated manipulator.

FIGS. 6a and 6b show grippable sample collection apparatus 110 a further embodiment of this invention. Grippable sample collection apparatus 110 consists of modified tubular chamber 112 and closure 118. Closure 118 is similar to closure 14 shown in FIG. 1.

Modified tubular chamber 112 has a closed end and an open end shaped to receive and be sealed by closure 118. Said modified tubular chamber is preferably constructed of a substantially transparent material such as glass or a substantially transparent barrier plastic such as that sold by E.I. Du Pont de Nemours Inc. under the tradename Selar Pa. Attachment collar 114 is a disk shaped feature formed or irremovably attached to the circumference of modified tubular chamber 112. Preferably, attachment collar 114 is located around the open end of said modified tubular chamber in which case it may be molded as part of said modified tubular chamber. If said attachment collar is not so located it may be irremovably bonded to the circumference of modified tubular chamber 112 with an adhesive.

As shown in FIG. 6b, attachment collar 114 facilitates the automated manipulation of grippable sample collection apparatus 110 because it allows robotic gripper 116, or similar manipulator, to grasp said grippable sample collection apparatus by attachment collar 114 and apply a force parallel to the axis of said apparatus without slipping. Automated equipment would often be required to apply force in such directions when, for example, inserting grippable sample collection apparatus 110 into a close tolerance sample transport rack or a primary tube sampling analyzer.

Figure 7:
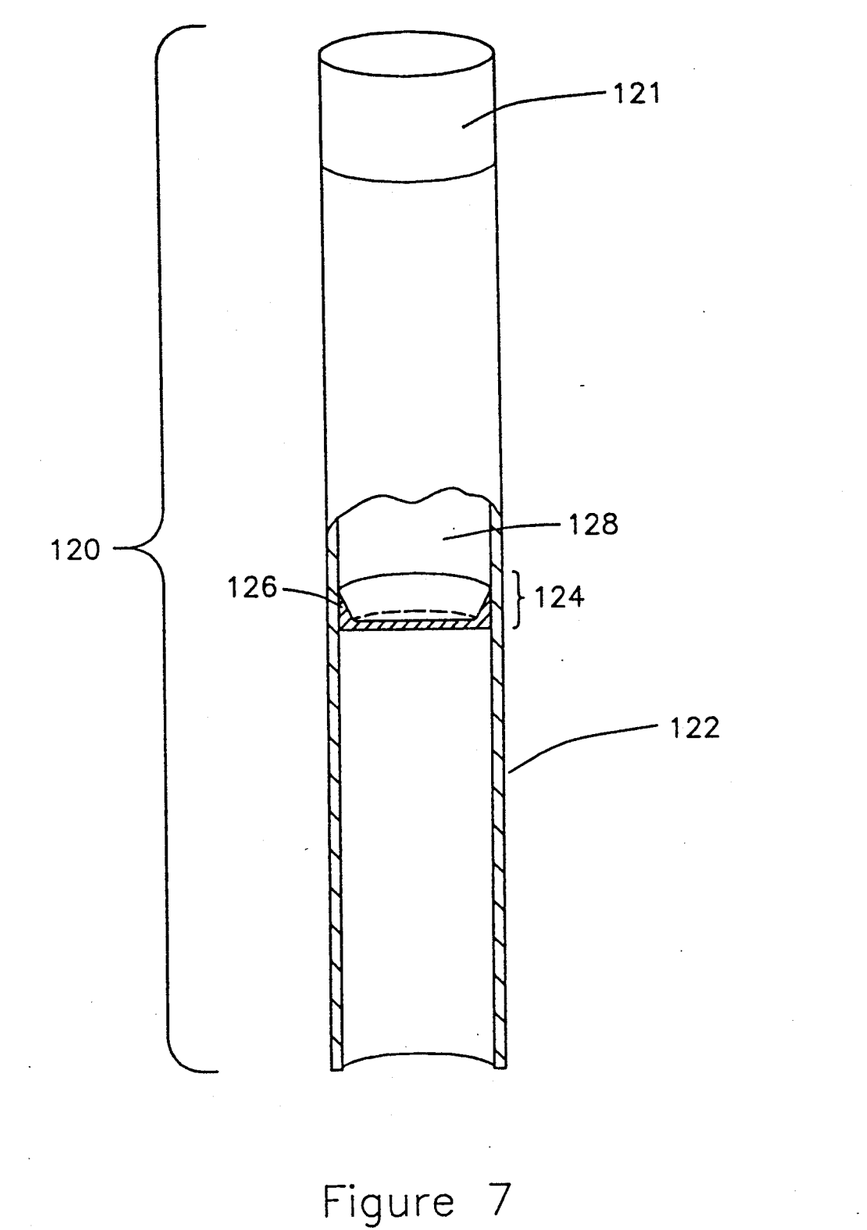
FIG. 7 shows a sectional view of a variable volume sample collection apparatus.

FIG. 7 illustrates variable volume sample collection apparatus 120, a further embodiment of this invention. Said variable volume sample collection apparatus consists of closure 121, tube 122, and bottom closure 124. Closure 121 is similar to closure 14 shown in FIG. 1.

Tube 122 has one end shaped to receive and be sealed by closure 121 and has another end shaped to be sealed by bottom closure 124. In this embodiment, tube 122 is preferably formed from a substantially transparent, barrier plastic such as that sold by E.I. Du Pont de Nemours Inc. under the tradename Selar Pa.

Bottom closure 124 is a disk-shaped member which seals tube 122 opposite to closure 121. Said bottom closure is preferably constructed from a barrier plastic but the material of construction need not be substantially transparent. Bottom closure 124 is formed to incorporate sealing lip 126 which serves to hold said bottom closure in place inside tube 122 during assembly. Said sealing lip has a diameter slightly greater than the interior diameter of tube 122 such that it is slightly compressed when located inside said tube. Bottom closure 124 is made to seal and be irremovably attached to the inside diameter of tube 122 at some position along the length of said tube. Irremovable connection of bottom closure 124 to tube 122 can be achieved through ultra-sonic welding or bonding by adhesives.

The enclosed volume 128 defined by closure 121, tube 122 and bottom closure 124 is constructed to permit evacuation and thereby facilitate collection of blood by venipuncture. The draw volume of variable volume sample collection apparatus 120, that is the nominal volume of blood said apparatus collects, is determined by the volume of said enclosed volume 128 and, therefore, by the position of said bottom closure 124 along the length of tube 122. Advantageously, an infinite range of draw volumes can be achieved within the exterior dimensions of said variable volume sample collection apparatus and, as a result of this, instruments or automated sample handling machines designed to accommodate samples of varying volumes need only accommodate sample collection tubes of a single external size.

Figure 8A:
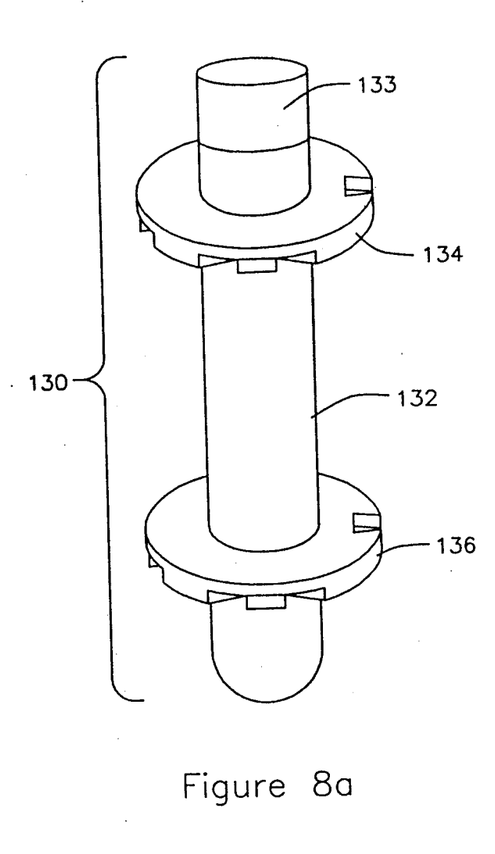
FIG. 8a shows a connectable sample collection apparatus.
Figure 8B:
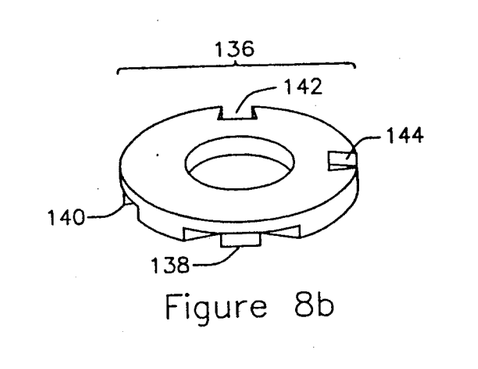
FIG. 8b is an enlarged view of an unattached self-connection feature of the connectable sample collection apparatus.

FIGS. 8a and 8b show connectable sample collection apparatus 130 the final embodiment of the present invention. Connectable sample collection apparatus 130 consists of tubular chamber 132, closure 133 and self-connection features 134 and 136. Tubular chamber 132 has a closed end and an open end shaped to receive and be sealed by closure 133 and is preferably constructed of a substantially transparent material such as glass or a substantially transparent barrier plastic such as that sold by E.I. Du Pont de Nemours Inc. under the tradename Selar Pa. Closure 133 is similar to closure 14 shown in FIG. 1.

In this embodiment, self-connection features 134 and 136 are identical, ring-like features which are irremovably attached to tubular chamber 132 around the circumference and near opposite ends of said tubular chamber. Preferably, said self-connection features are irremovably bonded to said tubular chamber by application of a suitable adhesive. Self-connection features 134 and 136 are constructed such that a multiplicity of connectable sample collection apparatus may be joined by interlocking the self-connection features present on each connectable sample collection apparatus. Because both self-connection features 134 and 136 are identical to each other, description of one self-connection feature will suffice to describe both.

As shown in FIG. 8b, self-connection feature 136 comprises four connection stations equally spaced about its circumference. These connection stations consist of two male connection stations 138 and 140, located adjacent to one another about the periphery of said self-connection feature, and two female connection stations 142 and 144. Because both male connection stations 138 and 140 and female connection stations 142 and 144 are located adjacent to one another, said self-connection features are polarized, that is they may only be connected one to another in certain orientations of connectable sample collection apparatus. Male connection stations 138 and 140 consist of fan-shaped tongues formed in relief on the underside of said self-connection feature. Female connection stations 142 and 144 consist of fan-shaped cavities formed into the topside of said self-connection feature. The construction of said male and female connection stations is such that the male and female connection stations of different tubes interlock and removably connect with one another. Self-connection feature 136 is preferably constructed from a ductile plastic material such as polyethylene.

Figure 8C:
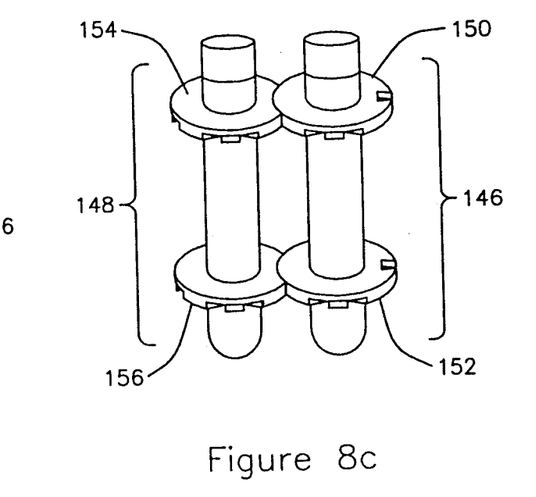
FIG. 8c shows two connectable sample collection apparatus connected together.

In use, a multiplicity of connectable sample collection apparatus 130 may be connected together. FIG. 8c shows two such connectable sample collection apparatus, first apparatus 146 and second apparatus 148, connected together. Aligning first apparatus 146 such that a male connection station on each of self-connection features 150 and 152 is aligned with and above a female connection station on self-connection fetures 154 and 156, followed by pressing said male connection stations into said female connection stations causes deformation of the fan-shaped tongues of the male connection stations and removably attaches first apparatus 146 to second apparatus 148. The attachment formed by the described operation is reversible and permits the separation of said first and second apparatus from each other.

The main benefit of connectable sample collection apparatus 130 lies in the flexibility afforded sample handling. Serial handling of samples, that is handling samples one at a time, permits the highest degree of flexibility in sample handling but may not permit optimal allocation of effort when the same operation must be performed on a large number of samples. Conversely, batch handling of samples, that is handling samples in groups, may minimize the operations required to process a group of samples but it forces a single sample within the batch to wait for the conclusion of the entire batch operation in order to complete processing. Optimal sample handling, that is a situation where processing time for each single sample is minimized, is likely a mixture of serial and batch sample handling. Connectable sample collection apparatus 130 permits a group of samples to be batched together or separated for serial processing as is optimal. A specific example may be an automated sample handling device designed to optimally process serial samples. If this device is designed to accept samples from and discard sample to batch collection interfaces, then connectable sample collection apparatus 130 would permit the automated sample handling device to break up batched samples presented to it thereby permitting optimal internal handling of the samples and then recombine said connectable sample collection tubes into batches for collection.

Since many changes can be made in construction of the above sample collection apparatus of this invention without departing from the scope thereof, it is intended that all matter contained in the above description or shown in the accompanying drawings shall be interpreted as illustrative and not in a limiting sense. Examples of embodiments which do not depart from the scope of this disclosure are: modifying the material employed in the layered construction of the tubular chamber such that shatter resistance, chromatic interference, or bio-degradability is provided; and the addition of blood clot activators or anticoagulants to the sample containers. Accordingly the invention is to be limited only by reference to the appended claims.

We claim:

1. Fluid collection apparatus comprising:
   a tubular first layer formed of a first material;
   a tubular second layer formed of a second material and attached to and substantially covering the first layer; and further including
   a protected label enclosed between the first and second layer for carrying indicia wherein the label carrying the indicia is made of a material differing from the materials of the first and second layers.

2. Fluid collection apparatus comprising:
   a tubular first layer formed of a first material;
   a tubular second layer formed of a second material and attached to and substantially covering the first layer;
   wherein the second layer includes a radially extending collar that includes mating means for attaching one collar directly to another collar without any other components.

3. Fluid collection apparatus comprising:
   a tubular first layer formed of a first material;
   a tubular second layer formed of a second material and attached to and substantially covering the first layer;
   wherein a portion of a surface of the first layer is roughened relative to the remaining portion of the surface thereby to facilitate coagulation of an entire specimen of blood contained in the fluid collection apparatus.

* * * * *